United States Patent
Eigen et al.

[11] Patent Number: 5,807,677
[45] Date of Patent: Sep. 15, 1998

[54] METHOD FOR DIRECT IDENTIFICATION OF FEW NUCLEIC ACID STRANDS

[75] Inventors: Manfred Eigen, Göttingen, Germany; Rudolf Rigler, Danderyd, Sweden

[73] Assignee: Max-Planck-Gesellschaft zur Förderung der Wissenschaften e.V., Munich, Germany

[21] Appl. No.: 574,916

[22] Filed: Dec. 19, 1995

[30] Foreign Application Priority Data

Mar. 10, 1995 [DE] Germany ................ 195 08 366.0

[51] Int. Cl.⁶ .............. C12Q 1/68; C12P 19/34; C07H 19/00; C07H 21/02
[52] U.S. Cl. .............. 435/6; 435/911; 435/912; 536/22.1; 536/23.1; 536/24.3; 536/25.3
[58] Field of Search ............ 435/6, 91.1, 91.2; 536/22.1, 23.1, 24.3, 25.3, 25.32

[56] References Cited

U.S. PATENT DOCUMENTS 4,656,127  4/1987  Mundy ........................... 435/6
5,252,743  10/1993  Barrett et al. ................ 548/303.7

FOREIGN PATENT DOCUMENTS 0531027  3/1993  European Pat. Off. .

OTHER PUBLICATIONS

Kinyo et al. "Ultrasensitive Hybridization Analysis Using Fluorescence Correlation Spectoscopy". Nucleic Acids Research, vol. 23, No. 10 pp. 1795–1799, 1995.

*Primary Examiner*—Ardin H. Marschel
*Assistant Examiner*—Jezia Riley
*Attorney, Agent, or Firm*—Harness, Dickey & Pierce, P.L.C.

[57] ABSTRACT

A method for the direct identification of few, preferably single nucleic acid strands of a specific target sequence (10) in a test solution comprising the following steps:

a) Preparation of a reference solution with a mixture (11) of different, short primers (12, 13, 14) each with a so-called antisense-sequence (a', b', c') complementary to a section (a, b, c) of the target sequence (10), and marked with one or more dye molecules, b) mixture of the reference solution with the test solution and incubation of this mixture (15) under conditions allowing hybridization of the primers (12, 1, 14) with the nucleic acid strands to be identified, and then c) identification of the target sequence (10) in the incubated solution (15) by discriminating few, preferably one of the nucleic acid strands to be identified to which one or more primers (12, 13, 14) have hybridized against the background of the non-hybridized primers (12, 13, 14).

28 Claims, 2 Drawing Sheets

METHOD FOR DIRECT IDENTIFICATION OF FEW NUCLEIC ACID STRANDS

BACKGROUND OF THE INVENTION

The present invention relates to a method for a direct identification of few, preferably single nucleic acid strands of a specific target sequence in a test solution.

The invention also relates to a device to carry out this method and a test solution used for this purpose.

It is generally desirable if DNA/RNA molecules of known, partly known and/or unknown sequences can be identified. Examples of such applications are genetic tests, analyses of laboratory experiments, e.g. within the scope of evolutionary biotechnology, or above all virus diagnostics. In all of these application cases there are often only a few or even individual nucleic acid strands of the specific sequence in the original test solution whereby these preferably have to be quantified.

A virus infection is at present generally proven by indirect methods, namely an immunoresponse from the infected host. The test poses a number of problems associated with this indirect method. These include the long latency period of the delayed immunoresponse, the time-consuming analysis, e.g. Elisa Test, and the possibility of a false-positive or false-negative immunoresponse.

There have thus been efforts to design a direct test with which the virus can be very specifically identified. The problems of a direct identification lie primarily in the requisite high sensitivity. In a borderline case it must be possible to identify a single virus particle in a cell extract or serum. The concentration of the nucleic acid strands to be identified are hereby in the range of $10^{-12}$ to $10^{-18}$ molar.

RELATED PRIOR ART

One method which was developed a number of years ago involves amplifying the individual or few nucleic acid strands to a concentration level suitable for conventional methods such as gel electrophoresis, the process of temperature gradient gels, sequencing, for example according to the Sanger Method or the Maxam-Gilbert technique. Polymerase chain reactions (PCR) or analog methods are available for this amplification. These are based on a specific replication of the nucleic acid sections to be identified. One hereby exploits the properties of DNA-polymerases, which can polymerise a single strand to a double-strand if they are provided with a short, double-stranded section as a primer. The nucleic acid strands containing a sequence to be amplified are mixed with two chemically synthesized oligonucleotides originating from the end areas of the sequence to be amplified and which are strand-specific, i.e. complementary to one of the two DNA strands.

On the one hand such methods are very time-consuming; not only do the PCR reactions have to be carried out but these are then followed by a umber of further analyses so as to be able to at least quantitatively conclude the presence of the desired sequence in the test solution. Moreover, certain short-chain nucleic acid sequences with a length of approx. 15–20 nucleotides have to be provided which are exactly complementary to a corresponding section of the sequence to be detected. Such an exactly complementary short-chain nucleic acid section is generally called an "antisense sequence" or "primer".

Apart from the time involved, this method also has the disadvantage that only those nucleic acid sequences can be identified where at least a short section of the sequential sequence at both ends is known so that the corresponding primer can be provided. If the nucleic acid strands to be identified are RNA molecules, these first have to be transcribed into a DNA copy by means of an RNA-dependent DNA polymerase before the PCR method can be employed.

On account of the in some cases numerous procedural steps, this method displays a number of error sources since the single polymerases can only incorporate the "correct" complementary nucleotide during polymerisation with a certain probability, so that here again, the possibility of false-positive and false-negative test results cannot be excluded.

A further method consists of directly visualizing the sequence to be identified, which means that naturally this sequence first has to be clearly distinguishable from alternative sequences. A newly developed method to identify and count individual molecules is the fluorescence correlation spectroscopy described in WO 94/16313, hereinafter referred to as the FCS method. The publication quoted explains how single DNA/RNA molecules marked with dye can be identified by FCS in a very small probe volume in the range of 0.1–10 fl provided the molecule to be identified either differs significantly from alternative molecules in the probe volume or has been isolated.

In the PCR method already mentioned above, two primer sequences are required of which one is complementary to the start region of the plus strand and the other complementary to the start region of the minus strand. The sequence section between the positions of the two primer sequences is then amplified. With the FCS method all that is required is a specific primer sequence marked with a fluorescence dye. This hydribizes directly on to (single-stranded) RNA sequence to be detected or to a strand of the melted DNA sequence. In this way the marked primers differ greatly from the free primers in both their charge characteristics and their mobility and can be directly detected by FCS without further amplification.

The measuring principle with FCS is based on the fact that fluorogenic molecules can be measured in extremely diluted solutions by exposing a small volume element of the solution to the strong excitation light of a laser. Only those molecules of the corresponding excitation spectrum which are contained in the probe volume will be excited by the light. The emitted fluorescence light from this volume element is then imaged on a photomultiplier. If the solution has been diluted there will be significant fluctuations in the concentration of the molecules in the respective volume element.

A molecule which has once diffused into the volume element will leave this again according to its characteristic rate of diffusion after a mean period of time, which is however characteristic for the corresponding molecule, and will then no longer be able to be observed.

If the luminescence of one and the same molecule is now excited a number of times during its mean period of stay in the probe volume a number of signals can be recorded from this molecule.

In the case of diluted solutions the probability that a molecule which has diffused into the probe volume will be excited again before it leaves this volume is much higher that is the case for a newly arriving molecule.

In the aforementioned WO 94/16313 it is explained that on the basis of the measurement principle it is possible to record single molecules in diluted solutions. If the molecules to be identified are nucleic acid strands, a dye-marked primer whose diffusion behaviour in a free state differs from that of the target molecule in a bound state and which is complementary to a certain partial sequence of the molecule to be identified is added.

In order to reduce the in some cases very long measuring time, which depends on the diffusion rate of the molecules involved, the aforementioned publication describes various methods with which the molecules to be identified can be concentrated in probe volumes. In principle these methods are based on an exploitation of the different charges of free primers and primer-nucleic acid strand complexes so as to either separate the free primers from the complexes in a directional electric field, or exploit the different drift rates.

A different method to improve the specificity of the identification consists of using two different primers which are marked differently. The signals of the non-correlated, i.e. free primers, can then be efficiently suppressed by a temporal correlation of the fluorescence signals from the variously marked primers by means of electronic signal processing.

It is also explained that a lower-frequency electrical alternating field of, for example, 4 Hz produces an oscillation of the charged molecules through the probe volume so that the molecules are quasi focused, thus enabling only a single molecule or few molecules in the probe volume to be quantified.

The PCT publication quoted describes a number of application possibilities for FCS, but only deals with the device, the optical system and various molecule traps in more detail. However, it is also mentioned that single DNA/RNA strands can also be counted with the FCS apparatus using primers. The PCT application also pays particular attention to the measurement of physical parameters, whereby differently marked ligands are also used, which not only improve the intensity of the measuring signal but also increase the specificity. A cross-correlation technique is namely used for such differently marked probes so as to be able to determine further parameters such as the rotation speed of the molecule to be identified.

It is generally explained that electrophoretic separating processes, capillaries, continuous fields, etc. can be used to transpose a drift speed over the diffusion rate of the molecules involved. The primers and target molecules can be chosen in such a way that they display different charges and thus move differently in an electric field.

The FCS method thus has a number of advantages compared to the PCR method or analog methods. Firstly, the FCS method can be used directly for both single-stranded and double-stranded nucleic acid molecules. Since a number of pathogens are single-stranded RNA viruses, with the FCS method these do not firstly have to be transcribed to DNA, which has a positive effect on the time required for the analysis. Moreover, the FCS method is more direct, identifying the individual nucleic acids which otherwise first would have to be amplified when using the PCR method. This also leads to a noticeable difference in the time required.

In addition, the amplification process can be disturbed or hindered by certain substances so that the PCR method is not always reliable for natural samples.

However, just like the PCR method, the FCS method is susceptible to faults with respect to its specificity. Partial sections of a primer sequence, e.g., may also be complementary to sequences which are by chance similar to the target sequence. Primer sequences of lengths between 15 and 20 nucleotides are thus selected to achieve an adequate specificity of binding. However, it then has further to be ensured that the melting points of only partially complementary sequences are below the working temperature, in other words cannot be measured.

In the PCR method two primer sequences are used, whereby the probability that both sequences display faulty bindings is slight. However, the primers have to be used in much higher concentrations since they are consumed by the reaction.

With the FCS method the primer concentration only has to be high enough to enable a settlement to the nucleic acid strands to be identified within the measuring time.

These conditions greatly restrict the applicability of the method for small absolute quantities.

SUMMARY OF THE INVENTION

In view of the above, it is an object of the present invention to provide a method of the type mentioned at the outset, which overcomes the aforementioned disadvantage and difficulties and permits a fast and safe direct identification or proof of nucleic acid strands.

In accordance with the invention the object is achieved on the one hand by a method of the type mentioned at the outset and comprising the steps:

a) Preparation of a reference solution with a mixture of different, short primers each with a so-called antisense-sequence complementary to a section of the target sequence, and marked with one or more dye molecules;

b) mixture of the reference solution with the test solution and incubation of this mixture under conditions enabling hybridisation of the primer with the nucleic acid strands to be identified; and then c) identification of the target sequence in the incubated solution with an apparatus for optical analyses, designed to discriminate few, preferably one of the nucleic acid strands to be identified on which one or more primers have hybridized against the background of the non-hybridized primers.

The problem on which the invention is based is thus completely solved. Through the hybridisation of a number of primers with the target sequence, the local concentration of the primer, for example in the probe volume of the FCS method, is significantly increased if a target sequence with attached primers diffuses in the probe volume, this being seen as a "flash of light" in the registered fluorescence signal. The inventors of the present application have recognized that it is possible to use such a "cocktail" of primers since when identifying single nucleic acid strands, all that is important is to amplify the fluorescence signal. Sequences to which a primer has become attached "randomly", as it were, are now no longer shown as false-positive on account of the much weaker signal, unlike the known FCS method.

The specific reaction velocity of the hybridisation between primers and target sequences is generally below $10^{-6} M^{-1} s^{-1}$, so that even with primer concentrations of $10^{-9} M$ the reaction time exceeds a thousand seconds. If only a few copies of the target sequences itself are available, e.g. one strand per microliter, a direct identification would be impossible because in the quoted example there would be a surplus of free primer of many millions. Contributions of the bound fluorescence marker would be much too small to be registered by the FCS method.

However, this object is achieved in the invention by providing a cocktail of primer sequences which are complementary to various regions of the target molecule. Each primer sequence on average can be provided with a fluorescence marker, all of which consist of the same, though possibly also different fluorophors. This cocktail is provided in a solution of, for example, around $10^{-9}$M, corresponding to one molecule per femtoliter. With the FCS method, in which the "light trap" of the laser beam has a volume of approx. 0.2 fl, a "background noise" would thus be recorded which corresponds to the presence of a fluorescence marker for around 20% of the time. If a target molecule now enters the light or molecule trap there would be a sudden "illumination" of the fluorescence since there would now be, e.g. between 20 and 100 fluorescence markers in the light trap simultaneously. Whereas the marked target molecule would be completely lost in the mean intensity, it would appear in the fluctuation registration of FCS as a sort of "light bomb".

In principle this idea can also be used for tumour cells to enable a fast and direct detection of tumours. The fact that each tumour cell displays thousands of antigen determinants for antibodies can be used in this case. If the antibodies are now marked with dye a tumour cell to which antibodies have linked can be identified as a "flash lighting" with the aforementioned FCS method. This method also exploits the concentrating effect of antibodies marked with dye through attachment to the tumour cell. A tumour identification based on this idea would be an alternative application for the idea in accordance with the invention, whereby a number of differently dyed probes are used with a target object to which a large number of these probes could link or bind themselves. If the concentration of probes is kept so low that they appear in the observed probe volume with a statistical probability far below the number of probes on average linked to the target object, the concentration of the probes in the probe volume can be measured when a target object with linked probes enters the probe volume.

On the other hand, this object is achieved by a method of the type mentioned at the outset and comprising the steps:

1) hybridisation of at least some of the nucleic acid strands to be identified with an antisense strand which is marked with a number of dye molecules and is complementary to all or nearly all of the target sequence, and 2) identification of the target sequence with an apparatus for optical analyses designed to discriminate few, preferably one of the nucleic acid strands to be identified onto which an antisense strand has hybridized.

The object underlying the invention is also completely achieved by this method. The fluorescence signal is enhanced by marking the antisense strand with a large number of dye molecules so that such a double strand is also seen as a "light flash" in the registered fluorescence signal.

The hybridisation between the nucleic acid strand to be identified and antisense strand can either be carried out by producing the antisense strand separately and adding this to the test solution, in the same way as the method using the short primers, an then subjecting this to a suitable tempering process.

Alternatively, it is also possible to produce the dyed double strand of nucleic acid strand to be identified and antisense strand through a direct polymerisation of the nucleic acid strand to be identified, whereby dyed nucleic acid (or analog) mononucleotides are used. Marked UTP's are preferably used in this case. If the double strand produced in this manner, which is marked with a large number of dye molecules, cannot be identified against the background of the free, similarly marked mononucleotides, suitable separating methods must be employed before the solution containing the marked double strand is placed in an FCS apparatus, as will be described in more detail below.

In one embodiment of the first method in accordance with the invention, complementary primer sequences are provided in step a) for different, preferably not overlapping sections of the target sequence whereby various primer sequences differ from one another in the sequential sequence of the nucleic acid (or analog) "building blocks".

The advantage of this is that the number of primer sequences binding to a target sequence is very large, so that there is a high concentration of the primer sequences in the probe volume, guaranteeing a greater certainty against false-positive measurement results due to accidentally matching single primers.

It is then preferred if in step a) primers of different sequence lengths, i.e. with different numbers of nucleic acid (or analog) mononucleotides per primer, are provided whereby the primers preferably display a sequence length of between 10 and 50, preferably 15 and 20 mononucleotides.

These different primer lengths consider advantageously the secondary structures of the nucleic acid strands to be identified. Short-stranded primers would be used against single-stranded sections of the nucleic acid strands whereas longer primer sequences would be used, for example, against double-stranded sections, which would first have to be melted by a corresponding temperature selection, whereby the primer would then compete with the development of the secondary structure. On account of the large number of elements the binding between long-chain primers and corresponding sections of the target sequence is hereby so great that the primer binding primarily occurs before the development of the secondary structure. It could be shown that primer with a sequence length between 15 and 20 elements on the one hand enters into a sufficiently specific binding with complementary sections of the target sequence, and on the other it does not allow any random, unspecific bindings.

In a further development it is then preferred if primer with 10 to 200, preferably 20 to 100, different sequences are provided.

In this way between 300 and 2,000 complementary mononucleotides could be attached to the target sequences, which as virus-RNA, for example, display a sequence length of between 4,000 and 10,000 elements, so that during such a hybridisation on average they take up the maximum number of primers which can be bound. The advantage of this is that there is a very strong concentration of primers, and thus an exact increase in the fluctuating fluorescence signal when such a complex of target molecule and primers enters the probe volume, thus further improving the measuring accuracy.

It is generally preferred if the primer is produced through direct synthesis, for example using a nucleic acid synthesizer.

This has the advantage of being an absolutely safe method of providing the various oligonucleotides (primers). although this method is time-consuming, it excludes a possible presence of the overall target sequence within the "cocktail" offered and thus a false display of the target sequence. Overlapping primer sequences can also be avoided, thus permitting selective marking. However, the precise target sequence must be known.

On the other hand, it is preferred if the primers are produced through replication or transcription of the target sequence in the presence of nucleic acid (or analog) mononucleotides which have been marked with dye molecules, whereby the replication or transcription products are then out into partial sequences which are used as primers.

The advantage of this method is that it is much faster, but the cocktail still contains the target sequence at the beginning of the process, though this does not have to be precisely known.

It therefore has to be ensured that during cutting the target sequence is destroyed to prevent a false display. This cutting of the replication or transcription products can be carried out mechanically by employing shearing forces which destroy the products.

On the other hand it is possible to expose the replication or transcription products to the effect of specific and/or unspecific cutting nucleases for a certain period of time so that they are digested into primers.

The advantage of this is that this digestion can be temporarily controlled to produce primers with the desired mean length.

On the whole it is preferred if the replication or transcription products are produced by the polymerase chain reaction technique, an analog method or with the aid of other specific RNA or DNA polymerases.

These are well established methods which can be employed advantageously to produce the primer from the target sequence. In this manner primer can be advantageously produced against target sequences whose sequence succession is only partly known or completely unknown. All that is necessary is that the ends of the target sequences are known or that known sequence sections are synthesized to completely unknown sequence sections so that the primers necessary for the PCR method can be provided. The section of the target sequence between the two primers does not have to be known in the succession, the correct primers for the analysis are "automatically" produced, as it were, so that new viruses can also be looked for.

It is furthermore preferred if short DNA strands are produced with a DNA synthesizer which display sections of the target sequence, with these DNA strands are then transcribed, for example with the T7 polymerase, and the transcription products used as primer.

The advantage here is that RNA primer can be produced in a known manner, which can then be used in a cocktail in accordance with the invention against an RNA target sequence to be identified without the complete sequence succession of the target sequence having to be known.

It is generally preferred if DNA, RNA or PNA sequences are used as primers.

The advantage of this is that DNA and RNA target sequences can be proven, whereby the possible use of positively charged PNA sequences which display a peptide-like back-bone and—unlike RNA and DNA—are thus not negatively charged permits an electrophoretic separation between free and complexed primers. PNAs can also be given a positive charge by linking a positive residual group, thus further facilitating the separation.

It is furthermore preferred if in step b) the mixed solution is incubated at a temperature which is so high that tertiary and secondary structures in the target sequence melt, so low that the specific bindings between primer and target sequence do not melt and so high that unspecific bindings between primer and target sequence melt.

This permits an advantageous solution to an important problem of marking. The specific reaction velocity for the attachment of primer sequences is generally below $10^6 M^{-1} s^{-1}$ so that primer concentration of $10^{-9}M$ which is preferably used, reaction times of over 1,000 seconds already occur. These values depend greatly on the temperature since the secondary structure of the target sequence has to melt before the primer sequences can bind. On the other hand, one has to work at temperatures below the melting point of the primer binding, whereby the temperature should be directly below this melting point to exclude unspecific false attachments.

From all of this it follows that the marking of the target sequences with the primer cocktail is preferably achieved through a precisely specified tempering or annealing process which quantitatively takes the quoted melting points into account.

In a further development it is hereby preferred if the primer is used in great surplus compared to the target sequence, whereby after successful incubation the free primers can be separated from the hybridized target sequences.

The advantage here is that there is initially a saturation of the hybridisation at higher primer concentrations and that the unreacted primer is then separated.

This can be achieved very simply by electrophoresis if positively charged PNA sequences are used as primer.

The identification of the target sequence which has been hybridized with primer can be carried out in step c) by fluorescence spectroscopy with random time resolution, though this must be able to detect very small fluorescence signals down to single photon recording in a very small volume element. It is hereby important that the temporal resolution must ensure that the signals from free primers clearly differ from those which originate from the primers which have been concentrated by the target sequence.

This is preferably carried out by a correlation fluorescence spectroscopy whereby a very small volume element, preferably 0.1–20 fl of the incubated solution, is exposed to the excitation light from a laser which excites the primers in this probe volume to emit fluorescence light, whereby the fluorescence light emitted from the probe volume is measured with a photo-detector and a correlation drawn between the temporal change in the measured emission and the relative rate of diffusion of the molecules involved, so that with a correspondingly stronger dilution, individual molecules can be identified in the probe volume. It is them preferred if an electric field is used to increase the drift speed of the target sequences which have been hybridized with primers above the rate of diffusion.

Since a large DNA or RNA molecule diffuses relatively slowly it has to be concentrated with special methods in the light trap. In the event of normal diffusion, assuming a diffusion coefficient, of $5 \times 10^{-8}$ cm$^2$/s, such as has been measured for M13-phages, the mean time for diffusion of a target sequence in a light trap with a diameter of 0.5 μm is around $10^{-10}$ c$^{-1}$ seconds, whereby c is the molar concentration of the target sequence. With c=$10^{-15}$M the diffusion time would already be one day.

Although the diffusion time can be reduced by enlarging the spatial element of the light trap, there are limitations since the background noise increases by the third power of the radius of the spatial element.

One effective method is the aforementioned increase in the drift speed using electric fields, thus advantageously reducing the measuring time.

It is hereby preferred if a capillary electrophoretic separation of free primers and target sequences which have been hybridized with primers is carried out, whereby a capillary with a tip opening of less than 0.01 mm is placed in front of the probe volume and a continuous electric field generated in the capillary which moves the target sequences which have been hybridized with primer and are negatively charged, towards the probe volume.

This is an advantageous method of using an extended capillary, a so-called Neher capillary, such as is described in the article "The Patch Clamp Technique", E. Neher and B. Sakmann, in Scientific American, March 1992, Pages 44–51. It is already known from WO 94/16313, mentioned at the outset, that a field of approx. 1 kV/cm can be generated in such a capillary, leading to a velocity of migration of approx., 1 mm/s.

A quadropole or radial ion trap can also be used in place of the capillary, whereby the latter is particularly effective. This consists of a "point-shaped" tip (e.g. Neher capillary) surrounded by an annular electrode with a diameter of, e.g., 1 cm. The field in this case is a continuous field, the tip of the capillary has a positive charge. The negatively charged target structure accumulates in the inhomogeneous field at the tip. Here there is an equilibrium between accumulation through migration in the field and removal through diffusion. The slowly diffusing target structures accumulate up to $10^3$-times stronger than their low-molecular primer.

On the other hand it is preferred if in step c) a high-frequency, inhomogeneous alternating electrical field is used which induces in the target sequences a dipole moment which migrates as such in the inhomogeneous field.

This is an advantageous method of overcoming a significant disadvantage of capillary electrophoretic separation or radial ion traps since it avoids the additional accumulation of unmarked primers.

In the article "Structure and kinetic properties of poly-electrolytes in solution, determined from relaxation phenomena in electric fields", M. Eigen and G. Schwarz, in "Electrolytes", Pergamon Press 1962, it was shown that rod shaped poly-electrolytes and in particular nucleic acids have an electrical polarizability resulting from a shift in the ion cloud relative to the poly-ion in the electric field. There are very large induced dipole moments for DNA in partiicular, which with field strengths of $10^3$ volts/cm already lead to a complete alignment in the field. The relaxation time for the polarisation is around one microsecond so that it is possible to work with high-frequency alternating fields of around $10^5$ to $10^6$ Hz. The alignment takes place within a range between milliseconds and seconds.

In other words, high-frequency alternating fields induce strong dipole moments in nucleic acids and this can be displayed through a change in the conductivity of a solution containing nucleic acids treated in such a manner. However, this also means that nucleic acids in an inhomogeneous, high-frequency field migrate towards the higher field strength, which has been exploited in the invention to concentrate the marked target sequences in the probe volume since a dipole in the inhomogeneous field migrates towards the higher field strength, which can be located within the probe volume.

A radial electrode arrangement is employed for this purpose consisting of an electrode tip mounted in the light trap and an annular counter electrode.

BRIEF DESCRIPTION OF THE DRAWINGS

Further advantages arise from the description and enclosed drawings.

It is understood that the aforementioned and subsequent features can be used not only in the respective combinations specified herein, but also in other combinations or alone without going beyond the scope of this present invention.

Figure 1:
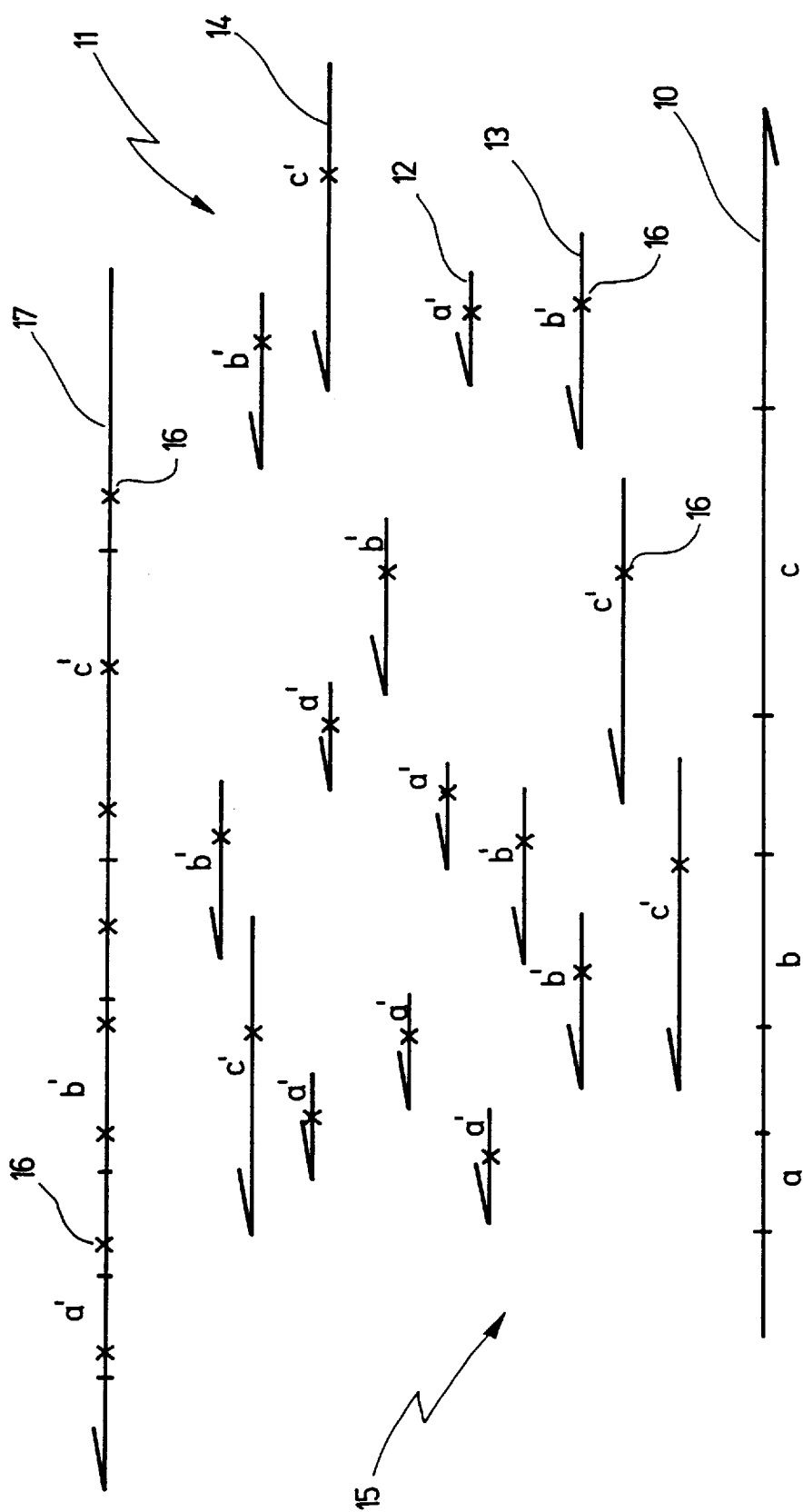
Figure 2:
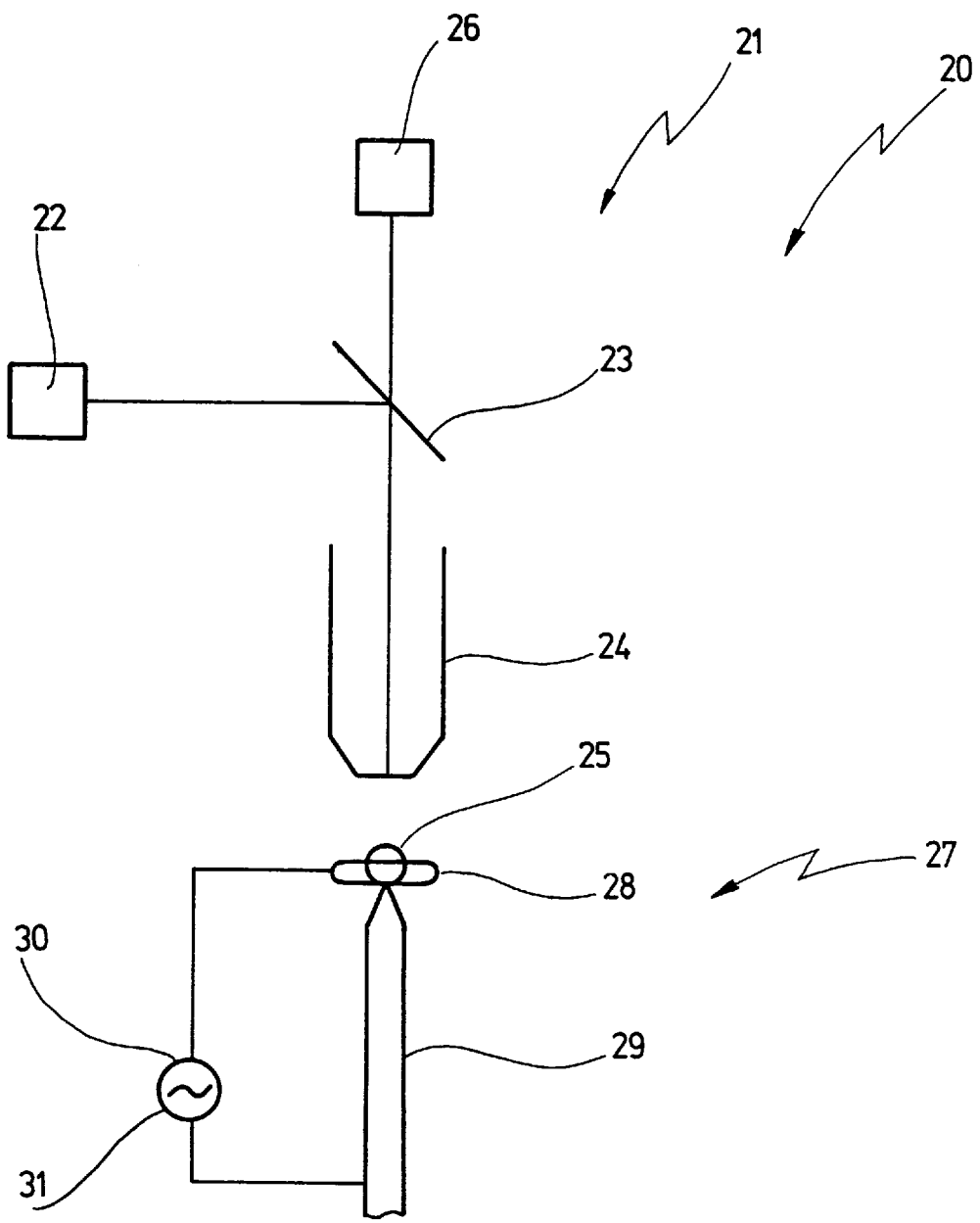

One embodiment of the invention is shown in the drawing and will be explained in more detail in the following:

FIG. 1 a simplified, diagrammatic representation of an incubation solution with target sequence and primers; and FIG. 2 a simplified, diagrammatic representation of an apparatus for optical analysis with an electric molecule trap, not shown to scale, which employs a high-frequency, inhomogeneous electric alternating field.

DETAILED DESCRIPTION OF A PREFERRED EMBODIMENT

FIG. 1 shows a diagrammatic view of a nucleic acid strand in the form of a target sequence 10, where individual, selected sequence sections are marked a, b and c.

Apart from the target sequence 10, a mixture 11 of primers 12, 13 and 14 is also shown which are located together with the target sequence 10 in an incubation solution 15.

The primer or oligonucleotide 22 displays a sequence a' which is complementary to section a, whereas primers 13 and 14 display complementary sequences to sections b and c.

The primers 12, 13 and 14 are each marked with one or more dye molecules 16, which emit a fluorescence light if correspondingly excited. The dye molecules 16 are shown in FIG. 1 by crosses.

Instead of a number of primers 12, 13, 14, a more or less complete antisense strand 17 can also be sued or a double strand can be produced through polymerisation of the target sequence 10 which is then marked with a number of dye molecules 16 and is complementary to the complete target sequence 10.

If the solution 15 is incubated at a temperature which is high enough to melt possible secondary structures of the target sequence 10, but low enough not to melt a specific binding between primers 12, 13 and 14 and the corresponding sections a, b and c of the target sequence 10, the primers 12, 13 and 14 hybridize to the target sequence 10. The incubation temperature must be sufficiently high to melt unspecific binding between primers 12, 13 and 14 and the target sequence 10.

In this way a solution 15 is produced in which the target sequence 10 or the few target sequences 10 each carry a number of primers 12, 13, 14, whereby the primers display a sequence length between 15 and 20 elements and a total of 20 to 100 different primers 12, 13, 14 are provided.

The primers 12, 13 and 14 can be produced either through direct synthesis, e.g. with a nucleic acid synthesizer, whereby short, dye-marked DNA strands can be produced with a DNA synthesizer which display the sections a, b or c of the target sequence 10. These DNA strands are then transcribed e.g. with the T7 polymerase, and the transcription products used as primers 12, 13, 14. This production method for the mixture 11, referred to as the "cocktail", assumes that the sections a, b and c in the sequence are known.

If, on the other hand, nucleic acid strand 10 with partly known or completely unknown sequence is to be used as target sequence, the primers 12, 13 and 14 are produced by replication or transcription of the target sequence in the presence of mononucleotides marked with dye molecules. This can be carried out by employing the polymerase chain reaction technique, an analog technique or with the aid of a DNA or RNA polymerase, e.g. the T7 polymerase, a reverse transcriptase, etc.

The replication or transcription products are then cut into partial sequences using either a mechanical method or specific and/or unspecific cutting nucleases to digest the products into primers. Naturally, it must hereby be ensured that the mixture 11 contains none of the target sequences which originally served as a basis for the transcription/replication so as to avoid any false-positive displays.

Both RNA and DNA molecules can be used as target sequence 10 and primers 12, 13 and 14. PNA molecules which can be given a positive charge so that the free primers 12, 13, 14 can be electrophoretically separated from the target sequences 10 with bound primers 12, 13, 14 can also be used as primers 12, 13 and 14.

If the antisense strand 17 is used this can either be added to the test solution, whereby a corresponding tempering process ensures the formation of double strands. On the other hand it is also possible to add mononucleotides marked with dye to the target sequence 10 and to polymerize the target sequence 10 to a double strand of target sequence 10 and antisense strand 17 using a polymerase. The specificity with respect to the target sequence 10 to be identified is achieved by firstly adding to the target sequence 10 a specific oligonucleotide, which forms with the start of the strand of target sequence 10 a double-stranded region which then serves as primer for the polymerase. Different target sequences 10 can thus be selected for the polymerase through different primers. In this way the target sequence is polymerized to a double strand marked with a number of dye molecules.

Part of the incubation solution 15 is then placed in an apparatus for optical analysis, shown diagrammatically in FIG. 2 and marked 20, which is designed to discriminate few, preferably one of the nucleic acid strands to be identified on which one or more primers have hybridized against the background of the non-hybridized primers.

The apparatus 20 shown in FIG. 2 is an FCS apparatus, such as is known from WO 94/16313 mentioned at the outset. Please refer to this publication and the quotations therein for a more detailed description of the design and function of this FCS apparatus 21.

In a brief summary the FCS apparatus 21 comprises a laser 22, which illuminates a small probe volume 25, between 0.1 and 10 fl, via a beam splitter 23 and a confocal imaging optical system 24. This probe volume 25 is imaged via the confocal optical system 24 on a photodetector 24, and this is coupled to an electronic evaluation system for FCS analysis, not shown here.

The probe volume 25 covers a small part of the incubation solution 15, which is not shown in FIG. 2 for reasons of better clarity.

If the incubation solution 15 contains the aforementioned, dye-marked double strand, the free dye-marked mononucleotides may have to be electrophoretically separated before placing the incubation solution 15 in the apparatus 20. On account of the numerous dye molecules such a migrating double strand appears in the probe volume 25 as a light flash and can thus be identified. Since the added or produced antisense strand 17 only specifically "matches" the target sequences 10, such a light flash means that the nucleic acid strands to be identified do in fact display the target sequences 10.

In order to convey the target sequences 10 which have been hybridized with primers 12, 13, 14 into the probe volume 25 faster than if controlled by diffusion, FIG. 2 shows an electric molecule trap 27, which in the embodiment shown here consists of an annular electrode 28 and a Neher capillary 29 whose extended tip lies in the centre of the annular electrode 28.

If an electric voltage is now applied between the annular electrode 28 and Neher capillary 29, the target sequences 10 drift into the probe volume 25. If the primers 12, 13, 14 and target sequences 10 display different charges one simultaneously achieves an electrophoretic separation.

In the embodiment shown the voltage 30 is, however, an alternating voltage 31 which generates an inhomogeneous, high-frequency electric alternating field between the annular electrode 28 and the Neher capillary 29. The frequency of this alternating field is preferably in the range of a few hundred kHz.

This electric alternating field produces very large induced dipole moments, particularly with DNA, which with field strengths of $10^3$ volts/cm already lead to a complete alignment in the field. The relaxation time for the polarisation is around one microsecond. It is thus possible to work with high-frequency alternating fields of around $10^5$ to $10^6$ Hz whereby the alignment takes place between milliseconds and seconds. This effect is now exploited to concentrate the marked target sequence in the probe volume 25.

The electric molecule trap 27 hereby uses the electrode tip of the Neher capillary 29 which is arranged in the probe volume 25, whereby the electrode tip has a diameter of 1 $\mu$m. The annular counter electrode 25 on the other hand has a diameter of 1 cm.

The incubation solution 15, which is not shown in FIG. 2 for reasons of better clarity, fills the space between the two electrodes 29, 28. An inhomogeneous radial field whose field strength is proportional to 1/r is generated in this space when voltage 30, 31 is applied. With an electrode voltage of 10 volts a field strength of $10^5$ volts/cm is thus achieved at the tip if r=1 $\mu$m.

The dipole induced in target sequence 10 is drawn into this inhomogeneous field in the area of the highest field strength, in other words in the area of the probe volume 25.

Since the dipole moment obtained is proportional to the square of the length, whereby in the event of DNA the equivalent length is assumed, field strengths can be selected to which only long, marked nucleic acid strands, though not short primer sequences, respond. Since a high-frequency alternating field is applied, large rigid dipoles such as protein molecules do not react to the electric trap 27 either.

In this way it is thus possible to enrich the target sequence 10 with the marked primer sequences 12, 13, 14 using the cocktail and to shift this target sequence 10 which has been hybridized with primers 12, 13, 14 into the probe volume 25 of apparatus 20. The use of the cocktail hereby increases the intensity of the measured signal whereas the use of the electric molecule trap 27 significantly reduces the necessary measuring time since a drift speed is superimposed over the rate of diffusion.

With this new method, the new mixture 11 and the new device 20 it is thus possible to identify individual nucleic acid strands of known and/or unknown sequences within acceptable measuring times.

As the following consideration shows, the thermal effects which occur in the probe volume 25 are negligible:

With an electrical conductivity (and electrical field strength E the dissipated energy in the homogeneous case of a capillary of length l and diameter d is:

$$Q_{el} = \sigma E^2 l d^2 \pi/4$$

The electrical equivalent of heat is hereby approx. 0.2 cal/Ws. In order to remove $Q_{el}$ through heat dissipation from the liquid a stationary temperature gradient dT/dr is required, whereby it is assumed that the medium has a heat conductibility of $\lambda$:

$$0.2 \sigma E^2 l d^2 \pi/4 = \lambda l d\pi \frac{dT}{dr}$$

or:

$$\frac{dT}{dr} = \frac{\sigma E^2}{\lambda \cdot 20} d$$

In a typical example, if $\lambda$ is assumed for water with $10^{-3}$ cal/(cm degrees sec), whereby $\sigma < 10^{-3}$ Siemens and E=10 volts/cm, the temperature gradient is less than 0.5 degrees/ cm if the capillary has a diameter of 0.1 cm. Assuming that the main heat accumulation takes place in water and not in the capillary walls, a serum without excessive dilution should be able to be investigated directly.

Similar considerations can be made for the radial molecule trap 27. The field strength in the area of the electrode tip of the Neher capillary 29 is $10^5$ volts/cm, so that there is a temperature gradient of $10^5$ degrees/cm in the area of one $\mu$m, which however corresponds to an overheating of 10 degrees in the range of one micrometer.

Finally, it should be mentioned that the sensitivity of the measuring method can be further improved by using two or more fluorescent dyes and by carrying out a cross-correlation, as is generally known from the publication WO 94/16313 which has already been mentioned a number of times.

What we claim is:

1. A method for identification of a nucleic acid strand of a specific target sequence in a test solution, comprising the steps of:
   a) preparation of a reference solution with a mixture of different, short primers each with so-called antisense-sequence complementary to a section of the target sequence, and marked with one or more dye molecules,
   b) mixing the test solution with a reference solution comprising a mixture of different primers each with an antisense-sequence complementary to a section of the target sequence, and marked with one or more dye molecules, and incubating the mixture under conditions allowing hybridization of the primers with the nucleic acid strand to be identified, and
   c) identifying the target sequence in the incubated solution by discriminating a nucleic acid strand to which one or more primers have hybridized against the background of the non-hybridized primers, wherein the identification of the target sequence is carried out by detecting fluorescence signals with a temporal resolution, ensuring that the signals from free primers differ from those which originate from the primers which have been concentrated by the target sequence.

2. A method in accordance with claim 1, wherein complementary primer sequences are provided in the reference solution for different sections of the target sequence whereby the primer sequences differ from one another in the sequential sequence of their nucleotides or nucleotide analogs.

3. A method in accordance with claim 1, wherein primers of different length are provided in the reference solution.

4. A method in accordance with claim 1 wherein at least one primer with a sequence length of between 10 and 50 nucleotides is provided in the reference solution.

5. A method in accordance with claim 1, wherein primers with 10 to 200 different sequences are provided in the reference solution.

6. A method in accordance with claim 1, wherein at least one primer in the reference solution is produced through direct synthesis.

7. A method in accordance with claim 1, wherein at least one primer in the reference solution is produced through replication or transcription of the target sequence in the presence of nucleotides or nucleotide analogs which have been marked with dye molecules, whereby the replication of transcription product is then cut into a partial sequence which is used as the primer.

8. A method in accordance with claim 7, wherein the replication of transcription product is exposed to the effect of specific and/or unspecific cutting nucleases for a certain period of time so that it is digested into a primer.

9. A method in accordance with claim 7, wherein the replication or transcription product is produced by a method selected from the group consisting of the polymerase chain reaction technique (PCR technique), an PCR analog method and other methods utilizing specific RNA or DNA polymerases, and combinations thereof.

10. A method in accordance with claim 1, wherein at least one primer in the reference solution is produced by transcribing a dna strand which itself is produced with a DNA synthesizer and which displays a section of the target sequence.

11. A method in accordance with claim 1, wherein the primers are selected from the group consisting of DNA, RNA and PNA sequences, and combinations thereof.

12. A method in accordance with claim 1, wherein the incubation is at a temperature which is high enough that tertiary and secondary structures in the target sequence melt, and low enough that the specific binding between primers and target sequence do not melt and high enough so that unspecific binding between primers and target sequences melt.

13. A method in accordance with claim 1, wherein the primer is used in surplus compared to the target sequence.

14. A method in accordance with claim 13, wherein after successful incubation the free primers are separated from the hybridized target sequence.

15. A method in accordance with claim 14, wherein positively charged PNA sequences are used as primers and separation is carried out electrophoretically.

16. A method in accordance with claim 1, wherein the identification of the target sequence is carried out by a fluorescence correlation spectroscopy whereby a small volume element of the incubated solution, is exposed to an excitation light from a laser which excites the primers in this probe volume to emit fluorescence light, the fluorescence light emitted from the probe volume is measured with a photo-detector and a correlation is drawn between the temporal change in the measured emission and the relative rate of diffusion of the molecules involved, so that with a correspondingly stronger dilution, individual molecules can be identified in the probe volume.

17. A method in accordance with claim 16, wherein an electric field is used to increase the drift speed of the target sequence which has been hybridized with primers to above the rate of diffusion.

18. A method in accordance with claim 17, wherein a capillary electrophoretic separation of free primers and target sequence which has been hybridized with primers is carried out, whereby a capillary with a tip opening of less than 0.01 mm is placed in front of the probe volume and a continuous electric field generated in the capillary which moves the target sequence which has been hybridized with primers and is negatively charged, towards the probe volume.

19. A method in accordance with claim 17, wherein a quadropole or radial ion trap is used in which the tip of a capillary is surrounded by an annular electrode which generates an inhomogeneous field in whose maximum field strength area the probe volume lies.

20. A method in accordance with claim 17, wherein a high-frequency, inhomogeneous electrical alternating field is used which induces in the target sequence a dipole moment which migrates as such to the inhomogeneous field.

21. A method in accordance with claim 20, wherein the alternating field has a frequency of many hundreds of kHz (kilohertz).

22. A method for identification of a nucleic acid strand of a specific target sequence in a test solution, comprising the steps of:

1) hybridization of the nucleic acid strand to be identified with an antisense strand which is marked with multiple dye molecules and is complementary to all or nearly all of the target sequence, and 2) identification of the target sequence by discriminating the nucleic acid strand to be identified to which an antisense strand has hybridized.

23. A method in accordance with claim 22, wherein the hybridization between the nucleic acid strand to be identified and antisense strand is carried out using nucleotides or nucleotide analogs marked with dye through direct polymerization of the nucleic acid strand to be identified to a double strand comprising the nucleic acid strand to be identified and the antisense strand.

24. A method in accordance with claim 5, wherein the direct synthesis is carried out using a nucleic acid synthesizer.

25. A method in accordance with claim 10, wherein T7 polymerase is used for transcription.

26. A method in accordance with claim 5, wherein primers with 20 to 100 different sequences are provided in the reference solution.

27. The method of claim 16, wherein the small volume element of the incubated solution is 0.1 to 20 femto-liter.

28. A method in accordance with claim 4 wherein at least one primer with a sequence length of between 15 and 20 nucleotides is provided in the reference solution.

* * * * *

UNITED STATES PATENT AND TRADEMARK OFFICE
CERTIFICATE OF CORRECTION

PATENT NO. : 5,807,677
DATED : September 15, 1998
INVENTOR(S) : Manfred Eigen et al.

It is certified that error appears in the above-identified patent and that said Letters Patent is hereby corrected as shown below:

Column 13, line 61, claim 7,
    "of" should be --or--.

Column 13, line 65, claim 8,
    "of" should be --or--.

Signed and Sealed this

Twenty-second Day of June, 1999

Attest:

Q. TODD DICKINSON

*Attesting Officer*      *Acting Commissioner of Patents and Trademarks*